US012208234B2

(12) United States Patent
Allerup et al.

(10) Patent No.: US 12,208,234 B2
(45) Date of Patent: Jan. 28, 2025

(54) FLUSHING APPARATUS FOR USE WITH AN IV INFUSION SET AND AN IV INFUSION SET HAVING AN AUTOMATIC FLUSHING FUNCTION

(71) Applicant: Droplet IV ApS, Copenhagen (DK)

(72) Inventors: Tore Victor Chrom Allerup, Copenhagen (DK); Rasmus Fält, Ballerup (DK); Mads Bundgaard Nørløv, Copenhagen (DK); Mette Dahl, Copenhagen (DK); Marcus Borum Mølskov Bech, Charlottenlund (DK); Christoffer Junker Elmelund, Nuussuaq (GL); Niklas Rädel, Bagsværd (DK)

(73) Assignee: Droplet IV ApS, Copenhagen (DK)

( * ) Notice: Subject to any disclaimer, the term of this patent is extended or adjusted under 35 U.S.C. 154(b) by 0 days.

(21) Appl. No.: 18/406,991

(22) Filed: Jan. 8, 2024

(65) Prior Publication Data
US 2024/0252739 A1    Aug. 1, 2024

(30) Foreign Application Priority Data
Jan. 31, 2023   (DK) .............................. PA202370050

(51) Int. Cl.
*A61M 5/14*    (2006.01)
(52) U.S. Cl.
CPC ........ *A61M 5/1414* (2013.01); *A61M 5/1411* (2013.01); *A61M 5/1413* (2013.01); *A61M 2005/1403* (2013.01)
(58) Field of Classification Search
CPC .................. A61M 5/36; A61M 5/1411; A61M 2005/1403
See application file for complete search history.

(56) References Cited

U.S. PATENT DOCUMENTS 3,963,024 A * 6/1976 Goldowsky ............. A61M 5/40
604/254
4,173,222 A * 11/1979 Muetterties ........... A61M 5/162
604/126

(Continued)

FOREIGN PATENT DOCUMENTS

| CN | 106310437 | 1/2017 |
| CN | 106860949 | 6/2017 |

OTHER PUBLICATIONS

First Technical Examination Report with Search Report dated Aug. 30, 2023 from Danish Patent Application No. PA202370050.
(Continued)

*Primary Examiner* — Laura A Bouchelle
(74) *Attorney, Agent, or Firm* — Crockett & Crockett, PC; K. David Crockett, Esq.

(57) ABSTRACT

A flushing apparatus for use with an IV infusion set and an IV infusion set having an automatic flushing function. The IV set includes a rigid and/or non-collapsible flushing liquid chamber (3), that is connected directly by a flushing port (7) to a fluid flow path for the IV fluid at a flushing height (FH) and by a venting port (17) at a venting height (VH). When the level of IV liquid in the fluid flow path falls below the venting height (VH) the venting port (17) allows air from the fluid flow path to enter the flushing liquid chamber (2) and flushing liquid from the flushing liquid chamber (2) to enter the fluid flow path via the flushing port (7) when, during use of the IV infusion set the IV liquid level falls below the venting height (VH), thereby allowing the flushing liquid chamber (2) to be drained by gravity into the fluid flow path.

16 Claims, 5 Drawing Sheets

(56) References Cited

U.S. PATENT DOCUMENTS

| | | |
|---|---|---|
| 5,242,392 A | 9/1993 | Vaughn |
| 2019/0030237 A1 | 1/2019 | Begg |
| 2019/0290837 A1 | 9/2019 | Warta |
| 2020/0246535 A1 | 8/2020 | Boegh Jessen |

OTHER PUBLICATIONS

Second Technical Examination Report—Intention to Grant—dated Sep. 28, 2023 from Danish Patent Application No. PA202370050.

* cited by examiner

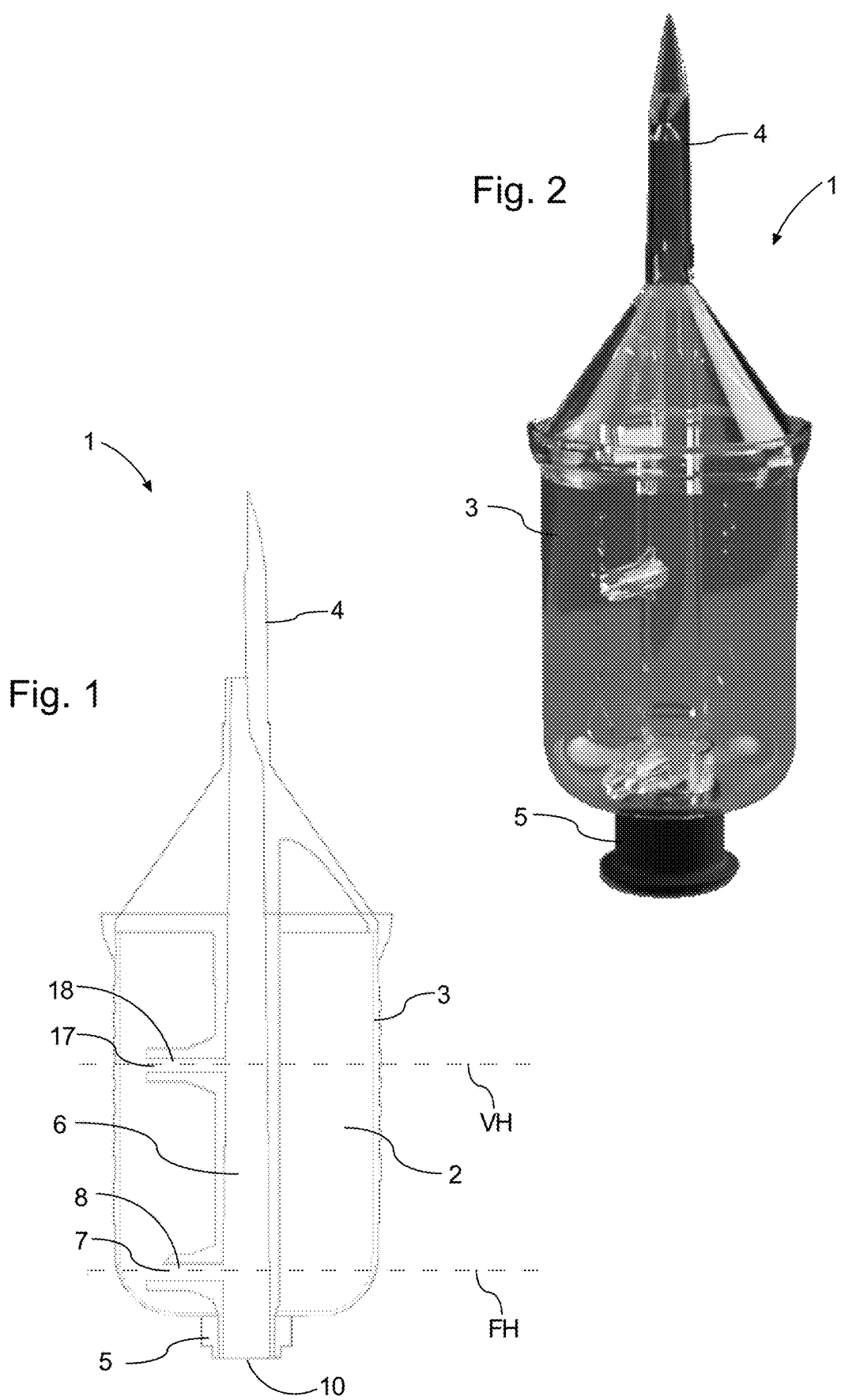

FLUSHING APPARATUS FOR USE WITH AN IV INFUSION SET AND AN IV INFUSION SET HAVING AN AUTOMATIC FLUSHING FUNCTION

This application claims priority to Danish Application PA 2023 70050, filed Jan. 31, 2023.

TECHNICAL FIELD

The disclosure relates to medical intravenous (IV) administration of fluids, specifically IV infusion sets and components thereof for medical applications.

BACKGROUND

IV liquid is nowadays administered to patients using an IV infusion set. Such an IV infusion set typically comprises an IV bag, a drip chamber downstream of the IV bag, and a tube provided with a roller clamp leading to a needle connector. The needle connected to the needle connector is either directly inserted into the patient or into an IV port that has been inserted into the patient beforehand. These IV infusion sets are either gravity-driven or gravity and pressure-driven using an IV pump.

A problem with the current way of administering intravenous medicine is that on average 15-25 mL (15-50%) of the dose remains in the infusion line as residual medicine. For example, mean residual volume of the administration sets was 13.1 mL and 16.7 mL for gravity and pump sets, respectively: "https://pharmaceutical-journal.com/article/opinion/patients-are-being-underdosed-we-need-new-guidance-on-small-volume-drug-infusions". In small-volume drug infusions, 10-32% of the prescribed dose may not be administered: https://www.bbraun.com/en/products-and-solutions/therapies/infusion-therapy/b-braun-for-safety/reducing_underdosing.html". Nurses will either perform a manual flush with saline or discard the infusion set with the result that the patient is being underdosed, placing patient safety at risk. Furthermore, delayed flushing increases the risk of phlebitis (chemical irritation of the vein) and occlusion of the vein catheter. This is a common complication seen in up to 30% of admitted patients, and necessitates replacement of the vein catheter, adding additional expenses for healthcare professionals in both time and costs as well as discomfort for the patients.

U.S. Pat. No. 5,242,392 discloses an IV piggyback tubing flush apparatus that includes a flush chamber attached to an intravenous (IV) set on the vertical tube and located lower than an IV medication bag for following administration of medication with a flush solution of normal saline from the flush chamber, which flushes the medication from the IV tubing and from a venous access device that is inserted into the patient, thereby preventing clotting of the venous access device. The flush solution automatically follows administration of the medication. An air vent on the flush chamber and a separate air vent on the medication bag facilitates the flow of medication and flush solution through the IV tubing and the venous access device. The flush chamber is located lower than the medication bag. This IV piggyback tubing flush apparatus requires the user to ensure that the flush chamber is located lower than the medication bag, requiring an adapted rack or stand, and further, this apparatus requires two drip chambers, a flush chamber, and an additional bag with flushing liquid. Hence, this apparatus has the advantage of automatic flushing, but the apparatus is relatively cumbersome to set up and studies have shown that this complexity severely hampers patient safety. Further, this apparatus does not flush the complete flow path from the IV bag to the patient, typically leaving 7 ml of IV liquid (medicine) that is not flushed.

US2020246535 discloses a dual-chamber drip controlling device for intravenous infusion sets enabling spontaneous flushing and a method for flushing a dual-chamber drip controlling device, wherein the dual chamber comprises a flushing chamber configured as a closed compartment, the flushing chamber being fillable with flushing fluid; an administration chamber configured as a gravity-based drip chamber with an inlet and outlet; and two conduits, namely conduit A and conduit B connecting the administration chamber to the flushing chamber, wherein each fluid conduit is provided with restriction means for restricting passage from the flushing chamber to the administration chamber, the restriction means being openable so as to render the administration chamber flushable. Although this device allows for automatic flushing, it has the disadvantage that it is relatively complicated to manufacture since it requires at least two conduits and flow restriction means, as well as a drip chamber, hence making this apparatus relatively expensive to manufacture and complicated to use.

US20190290837A1 discloses a device for the delivery of liquid medicine in an intravenous (IV) delivery system. The device consists of a negative pressure chamber filled with saline solution that is used to flush all of the residual liquid medicine from a secondary liquid medicine delivery tube. The negative pressure chamber sits below the drip chamber attached to the secondary medicine bag and is attached to the secondary medicine delivery tube in such a way that when the liquid medicine from the delivery tube has flowed below the negative pressure chamber, the negative pressure chamber releases the stored saline to flush the liquid medicine from the secondary liquid medicine delivery tube. A terminal end 17 of an intersecting tube 16 sits in the center of a conical extension 24 at the bottom of the negative pressure chamber 20 that contains the stored saline, which means that there is a circumferential gap between the outer wall 18 of the terminal end 17 and the inner wall 28 of the conical extension 24. In the preferred embodiment, the terminal end 17 is 5 mm below the bottom 23 and down into the conical extension 24. However, tests have shown that the automatic release of the stored saline is not sufficiently reliable for professional medical use, since the automatic release relies on air from the drip chamber 12 entering the bottom of the negative pressure chamber 20, typically, through small air bubbles to break the capillary bond at the terminal end 17 and between the outside wall 18 and inside wall 28 of the conical extension 24.

SUMMARY

It is an object to provide an automatic flushing function for IV infusion sets that overcomes or at least reduces at least one of the drawbacks mentioned above.

According to a first aspect, there is provided an IV infusion set having an automatic flushing function, the IV infusion set defining at least partially gravity-driven fluid flow path for IV liquid that extends from a preferably collapsible IV liquid container for containing IV liquid and air that is, when in use, positioned at the highest height of the IV infusion set to a connector for connecting to a needle for insertion into a patient or to an IV catheter placed in a patient at a lower height, the IV liquid container 20 having an upper end and a lower end, the IV infusion set comprising a body defining a rigid and/or non-collapsible flushing liquid chamber for containing a flushing liquid and preferably containing the flushing liquid, the flushing liquid chamber having an upper end and a lower end, the flushing liquid chamber being a closed chamber, except for at least one flushing port at or near the lower end of the flushing liquid chamber and at least one venting port for allowing air from the fluid flow path to enter the flushing liquid chamber, the venting port being fluidically connected to the fluid flow path at a vent height VH, the at least one flushing port being fluidically connected to the fluid flow path at a flushing height FH, the flushing height FH being lower than the vent height VH, the at least one flushing port forming a permanently open fluidic connection between the flushing liquid chamber and the fluid flow path, the at least one venting port forming a permanently open fluidic connection between the flushing liquid chamber and the fluid flow path, and the flushing height FH being equal to or lower than the lower end of the IV liquid container for allowing air from the fluid flow path to enter the flushing liquid chamber via the venting port and simultaneously allowing flushing liquid from the flushing liquid chamber to enter the fluid flow path via the flushing port when, during use of the IV infusion set, the level of IV liquid in the fluid flow path has become lower than the venting height VH, thereby allowing the flushing liquid chamber to be drained by gravity into the fluid flow path.

When the IV liquid container has been emptied of IV liquid the remaining air from the IV liquid container will enter the flushing liquid chamber and displace the flushing liquid, thereby allowing spontaneous or automatic flushing of the components downstream of the flushing liquid chamber with flushing liquid after emptying the IV liquid from the IV liquid container, and thereby flushing out IV liquid from the downstream components of the IV infusion set and ensuring that practically all the IV liquid that was present in the IV liquid container at the start of the procedure enters the patient.

By providing an IV infusion set according to the first aspect a simplified workflow is provided for Healthcare Professionals, mainly nurses, with one less work process to be done in relation to IV medication. Thus, ensuring that IV flushing guidelines will be followed, and the patient is more likely to reach the full dose of medication and reduce flushing delay leading to the occurrence of phlebitis and occlusion, by securing sequential flushing after every IV dose. Simplifying the procedure saves time so Healthcare Professionals can allocate resources to improve general patient care.

The inventors have observed that the need for flushing is often unrecognized or neglected due to more urgent tasks in patient care and even when flushing is performed it is most often delayed or performed suboptimally, e.g. by using non-closed IV systems with a higher risk of introducing microbial agents into the bloodstream. These practices put patients at risk of increased treatment duration and stay in hospitals as well as catheter-related complications such as occlusion and phlebitis and the rare, but potentially fatal sepsis.

The IV infusion set according to the first aspect is a solution for ensuring automated, sequential flushing after every dose of IV liquid. The apparatus is simple and compatible with the current equipment, so it offers healthcare professionals an optimized workflow and saves Healthcare Professionals at least one patient visit each time an IV dose is infused. Investigations have shown that Healthcare Professionals save approx. 5 minutes with each IV infusion using the apparatus according to the first aspect. Healthcare guidelines state that flushing should be performed directly after every infusion, however, this demand is not easily compatible with the busy life in hospitals where Healthcare Professionals have to care for many patients and balance many tasks at the same time.

The IV infusion set according to the first aspect ensures that everyadministration of IV liquid is flushed, leading to more effective treatment and potentially shorter stay in hospital. At the same time, the automated, sequential flushing prevents residual medicine and the risk of phlebitis significantly. All this while saving manhours in the hospital.

By providing a dedicated venting port, it is ensured that the flushing procedure starts reliably.

According to a possible implementation form of the first aspect, at least one flushing port and/or the at least one venting port is an always open fluidic connection that directly connects the flushing port to the fluid flow path, preferably the at least one flushing port and the at least one venting port being formed by an opening in a wall separating the flushing liquid chamber from the fluid flow path.

According to a possible implementation form of the first aspect, the at least one flushing port and or the venting port forms one or more of:
  a permanently open fluidic connection without substantial flow restriction,
  a permanently open fluidic connection without flow control elements,
  a permanently open fluidic connection without valves,
  a permanently open fluidic connection comprising neither tubing nor piping.

According to a possible implementation form of the first aspect, the flushing liquid chamber is arranged inside the collapsible container with the at least one flushing port connecting directly to the IV liquid chamber in the collapsible container at a height at or close to the height of the lower end of the collapsible container.

According to a possible implementation form of the first aspect, the flushing liquid chamber is arranged at a height below the IV liquid container or inside the IV liquid container.

According to a possible implementation form of the first aspect, the IV infusion set comprises a flushing apparatus, the flushing apparatus comprising:
  the flushing liquid chamber, and
  a conduit forming a portion of the fluid flow path, an upper end of the conduit being fluidically coupled to an inlet coupling component for accessing an IV liquid container and for receiving a gravity-driven flow of IV liquid from the IV liquid container, a lower end of the conduit being fluidically connected to an outlet coupling component for coupling to a downstream component of the IV infusion set and for delivering an at least partially gravity-driven flow of IV liquid or flushing liquid to the downstream component, the at least one flushing port being fluidically connected to the conduit, preferably at or near the lower end of the conduit and the at least one venting port being fluidically connected to the conduit.

According to a possible implementation form of the first aspect, the conduit is formed by a collapsible body, preferably when the conduit is not at least partially surrounded by the flushing chamber.

According to a possible implementation form of the first aspect, a rigid and/or non-collapsible container defining the flushing liquid chamber and an element defining the conduit are connected to form a single unit.

According to a possible implementation form of the first aspect, the conduit extends through the flushing liquid chamber.

According to a possible implementation form of the first aspect, the IV set comprises a drip chamber below the flushing height FH.

According to a possible implementation form of the first aspect, a cross-sectional area of the venting port is smaller than a cross-sectional area of the flushing port.

According to a possible implementation form of the first aspect, the flushing chamber is prefilled to a given level, and wherein the venting height VH is below the given level.

In a possible implementation form of the first aspect, the highest height of the IV infusion set is formed by the IV liquid container, by the latter being suspended from e.g. a hook of an IV stand.

In a possible implementation form of the first aspect, the flushing liquid chamber is a closed volume, i.e. a volume that is unable to fluidically communicate with its surroundings.

In a possible implementation form of the first aspect, the flushing liquid chamber is formed by a rigid and/or non-collapsible body, so that the volume of the flushing liquid chamber does not change, or at least not substantially change during (normal/regular) use of the IV infusion set.

In a possible implementation form of the first aspect, the IV infusion set comprises a flushing apparatus, the flushing apparatus comprising: the flushing liquid chamber and a conduit forming a portion of the fluid flow path, an upper end of the conduit being fluidically coupled to an inlet coupling component for accessing an IV liquid container and for receiving a gravity-driven flow of IV liquid from the IV liquid container, a lower end of the conduit being fluidically connected to an outlet coupling component for coupling to a downstream component of the IV infusion set and for delivering an at least partially gravity driven flow of IV liquid or flushing liquid to the downstream component, the at least one flushing port being fluidically connected to the conduit, preferably at or near the lower end of the conduit.

In a possible implementation form of the first aspect, the conduit is formed by a collapsible body, preferably when the conduit is not at least partially surrounded by the flushing chamber.

In a possible implementation form of the first aspect, the rigid and/or non-collapsible container defining the flushing liquid chamber and an element defining the conduit are connected to form a single unit.

In a possible implementation form of the first aspect, the inlet coupling component is rigidly connected to an upper side of the body, and the outlet coupling element is rigidly connected to a lower side of the body.

In a possible implementation form of the first aspect, the flushing liquid chamber tapers towards its lower end.

According to a second aspect there is provided a flushing apparatus for use with an IV infusion set, the flushing apparatus comprising:

a rigid and/or non-collapsible flushing liquid chamber for containing a flushing liquid and preferably containing the flushing liquid, an inlet coupling component for accessing an IV liquid container and for receiving an at least partially gravity-driven flow of IV liquid from the IV liquid container, the inlet coupling component being arranged, when in use, at an upper end of the flushing apparatus and the IV liquid container preferably being an IV bag, an outlet coupling component for coupling to a downstream component and for delivering a gravity driven flow of IV liquid and flushing liquid to the downstream component, the outlet coupling component being arranged, when in use, at a lower end of the flushing apparatus and the downstream component preferably comprising a drip chamber, and a conduit fluidically connecting the inlet coupling component to the outlet coupling component, the flushing liquid chamber having an upper end and a lower end, the flushing liquid chamber being a closed chamber, except for at least one flushing port at or near the lower end of the flushing liquid chamber and at least one venting port for allowing air from the conduit to enter the flushing liquid chamber, the venting port being fluidically connected to the conduit at a vent height VH, the at least one flushing port forming a permanently open fluidic connection between the flushing liquid chamber and the conduit, the at least one venting port forming a permanently open fluidic connection between the flushing liquid chamber and the fluid conduit, the at least one flushing port being fluidically connected to the conduit at a flushing height FH and the flushing height FH being lower than the vent height VH, for simultaneously allowing air from the conduit to enter the flushing liquid chamber via the venting port and flushing liquid from the flushing liquid chamber to enter the conduit via the flushing port, when, during use of flushing apparatus, the level of IV liquid in the conduit has become lower than the venting height FV, thereby allowing the flushing liquid chamber to be drained by gravity into the conduit.

When the IV liquid container has been emptied of IV liquid the remaining air from the IV liquid container will enter the conduit and subsequently the flushing chamber through the venting port and displace the flushing liquid, thereby allowing an automated flush of the components downstream of the flushing liquid chamber with flushing liquid after emptying the IV liquid from the IV liquid container, and thereby flushing out IV liquid from the downstream components of the IV infusion set and attempting that almost of the IV liquid that was present in the IV liquid container at the start of the procedure enters the patient.

By providing an infusion apparatus according to the second aspect a simplified workflow is provided for Healthcare Professionals, mainly nurses, with one less work process to be done in relation to IV medication. Thus, ensuring that IV flushing guidelines will be followed, and the patient will receive the full dose of medication and reduce flushing delay leading to the occurrence of phlebitis and occlusion, by securing sequential flushing after every IV dose. Simplifying the procedure saves time so Healthcare Professionals can allocate resources to improve general patient care.

The inventors have observed that the need for flushing is often unrecognized or neglected due to more urgent tasks in patient care and even when flushing is performed it is most often delayed or performed suboptimally, e.g. by using non-closed IV systems with a higher risk of introducing microbial agents into the bloodstream. These practices bring patients at risk of increased treatment duration and stay in hospitals as well as catheter-related complications such as occlusion and phlebitis and the rare, but potentially fatal sepsis.

The flushing apparatus according to the second aspect is a solution for ensuring automated, sequential flushing after every dose of IV liquid. The apparatus is simple and compatible with the current equipment, so it offers the Healthcare Professionals an optimized workflow and saves Healthcare Professionals at least one patient visit each time an IV dose is infused. Tests have shown that Healthcare Professionals save approx. 5 minutes with each IV infusion using the apparatus according to the first aspect. Healthcare guidelines state that flushing should be performed directly after every infusion, however, this demand is not easily compatible with the busy life in hospitals where Healthcare Professionals have to care for many patients and balance many tasks at the same time.

The flushing apparatus according to the second aspect ensures that every patient gets the full dose every time, leading to more effective treatment and potentially shorter stay in hospital. At the same time, the automated, sequential flushing prevents residual medicine and the risk of phlebitis. All this while saving manhours in the hospital.

According to a possible implementation form of the second aspect, the conduit extends through the flushing liquid chamber.

According to a possible implementation form of the second aspect, the at least one flushing port is arranged closer to the lower end of the flushing liquid chamber than to the upper end of the flushing liquid chamber, the at least one flushing port preferably being arranged at or near the lower end of the flushing liquid chamber.

According to a possible implementation form of the second aspect, the at least one flushing port and/or the venting port comprises an opening in a wall of the conduit.

According to a possible implementation form of the second aspect, at least a portion of the conduit is inside a main tube that extends from the inlet coupling component to the outlet coupling component, and wherein the at least one flushing port and/or the at least one venting port is preferably connected to the main tube.

According to a possible implementation form of the second aspect, the inlet coupling component comprises an IV spike, and/or wherein the outlet coupling component comprises a port for receiving an IV spike.

According to a possible implementation form of the second aspect, the conduit, the inlet coupling component and/or the outlet coupling component are integrally formed with a body that defines the flushing liquid chamber.

According to a possible implementation form of the second aspect, the at least one flushing port and/or the at least one venting port is an always open fluidic connection that directly connects the flushing port to the fluid flow path, preferably the at least one flushing port and/or the at least one venting port being formed by an opening in a wall separating the flushing liquid chamber from the fluid flow path.

According to a possible implementation form of the second aspect, the at least one flushing port and the at least one venting port forms one or more of:
a permanently open fluidic connection without substantial flow restriction,
a permanently open fluidic connection without flow control elements,
a permanently open fluidic connection without valves,
a permanently open fluidic connection comprising neither tubing nor piping.

According to a possible implementation form of the second aspect, the apparatus comprises a fluid flow path for IV infusion liquid to pass through the apparatus, the conduit forming part of the fluid flow path.

According to a third aspect there is provided an IV infusion set comprising an apparatus according to the second aspect or any implementations thereof.

According to a fourth aspect there is provided IV bag comprising a collapsible infusion liquid chamber, the collapsible infusion liquid chamber having an upper end and a lower end, the IV bag comprising a container defining a rigid and/or non-collapsible flushing liquid chamber for containing a flushing liquid and preferably containing the flushing liquid,
the flushing liquid chamber having an upper end and a lower end,
the flushing liquid chamber being a closed chamber, except for at least one flushing port at or near the lower end of the flushing liquid chamber and at least one venting port for allowing air from the bag to enter the flushing liquid chamber, the venting port being fluidically connected to bag at a vent height VH,
the at least one flushing port being fluidically connected to the collapsible infusion liquid chamber at or near the lower end of the collapsible infusion liquid chamber and the at least one venting port being fluidically connected to the collapsible infusion chamber at a level above the flushing port, for simultaneously allowing air from the collapsible infusion liquid chamber to enter the flushing liquid chamber and flushing liquid from the flushing liquid chamber to enter collapsible infusion liquid chamber when, during use of IV bag, the level of IV liquid in collapsible infusion liquid chamber has become lower than at least one venting port, thereby allowing the flushing liquid chamber to be drained by gravity into the collapsible infusion liquid chamber.

When the IV liquid container has been emptied of IV liquid the remaining air from the IV liquid container will enter the flushing chamber through the flushing port and displace the flushing liquid, thereby allowing an automated flush of the components downstream of the flushing liquid chamber with flushing liquid after emptying the IV liquid from the IV liquid container, and thereby flushing out IV liquid from the downstream components of the IV infusion set and ensuring that almost of the IV liquid that was present in the IV liquid container at the start of the procedure enters the patient.

By providing an IV bag according to the second aspect a simplified workflow is provided for Healthcare Professionals, mainly nurses, with one less work process to be done in relation to IV medication. Thus, securing that IV flushing guidelines will be followed, and the patient will receive the full dose of medication and reduce the occurrence of phlebitis, by securing sequential flushing after every IV dose. Simplifying the procedure saves time so Healthcare Professionals can allocate resources to improve general patient care.

The inventors have observed that the need for flushing is often unrecognized or neglected due to more urgent tasks in patient care and even when flushing is performed it is most often delayed or performed suboptimally, e.g. by using non-closed IV systems with a higher risk of introducing microbial agents into the bloodstream. These practices bring patients at risk of increased treatment duration and stay in hospitals as well as catheter-related complications such as occlusion and phlebitis and the rare, but potentially fatal sepsis.

The IV bag according to the fourth aspect is a solution for ensuring automated, sequential flushing after every dose of IV liquid. The apparatus is simple and compatible with the current equipment, so it offers the Healthcare Professionals an optimized workflow and saves Healthcare Professionals at least one patient visit each time an IV dose is infused. Tests have shown that Healthcare Professionals save approx. 5 minutes with each IV infusion using the apparatus according to the first aspect. Healthcare guidelines state that flushing should be performed directly after every infusion, however, this demand is not easily compatible with the busy life in hospitals where Healthcare Professionals have to care for many patients and balance many tasks at the same time.

The IV bag according to the fourth aspect ensures that every patient gets the full dose every time, leading to more effective treatment and potentially shorter stay in hospital. At the same time, the automated, sequential flushing prevents residual medicine and the risk of phlebitis. All this while saving manhours in the hospital.

In a possible implementation form of the fourth aspect, the at least one flushing port and/or the at least one venting port is obstructed by a user destructible barrier, preferably a rupture disk, break-away seal, or puncture membrane, for preventing diffusion between the flushing liquid and the IV liquid.

In a possible implementation form of the fourth aspect, the flushing port and/or the venting port is arranged in a wall separating the infusion liquid chamber from the collapsible infusion liquid chamber.

The foregoing and other objects are achieved by the features of the independent claims. Further implementation forms are apparent from the dependent claims, the description, and the figures.

BRIEF DESCRIPTION OF THE DRAWINGS

In the following detailed portion of the present disclosure, the aspects, embodiments, and implementations will be explained in more detail with reference to the example embodiments shown in the drawings, in which:

FIG. 1 is a cross-sectional view of a flushing device according to an embodiment, FIG. 2 is an elevated view of the flushing device of FIG. 1.

DETAILED DESCRIPTION

Figure 3:
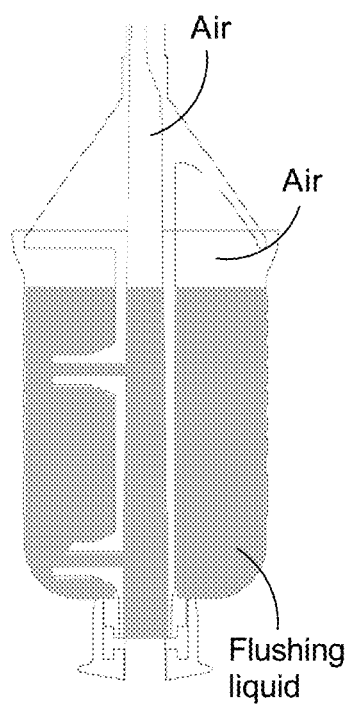
FIG. 3 is a cross-sectional diagrammatic representation of the flushing device of FIG. 1 filled with flushing liquid but not connected to any other parts of an IV set.

FIGS. 1 and 2 illustrate an embodiment of a flushing device 1 for use with a standard or bespoke IV infusion set. The flushing device 1 can also be used with intraoral feeding sets, parenteral delivery systems, and the like. FIG. 3 illustrates an IV infusion set for gravity infusions and pressure infusions.

The IV infusion set comprises a collapsible IV liquid container 20, preferably in the form of a collapsible bag 20, preferably made from transparent polymer sheet material, which is the highest component of the IV infusion set, e.g. by hanging the collapsible IV liquid container on a hook of an IV stand (not shown) using the hole 25 at the upper end of the collapsible IV liquid container 20. The lower end of the collapsible IV liquid container 20 is provided with an inlet port 23 and an outlet port 22 and the interior of the IV liquid container 20 comprises a collapsible infusion liquid chamber 21 that has an upper end and a lower end and that is at least partially filled with IV liquid and partially filled with air during or before use. In an embodiment (not shown), the IV liquid container 20 is not collapsible, e.g. a glass or plastic vial, and is provided with an air vent. The IV liquid container 20 is configured for containing an IV liquid and air. The IV liquid is typically a solution of medicine in water. The IV liquid container 20 is, during use, partially filled with IV liquid and partially filled with air. At the start of an infusion procedure, the amount of IV liquid (medical solution) to be infused to a patient is present in the IV liquid container 20, together with some air. At the end of the infusion period, the IV liquid container 20 contains no or very little IV liquid.

Figure 6:
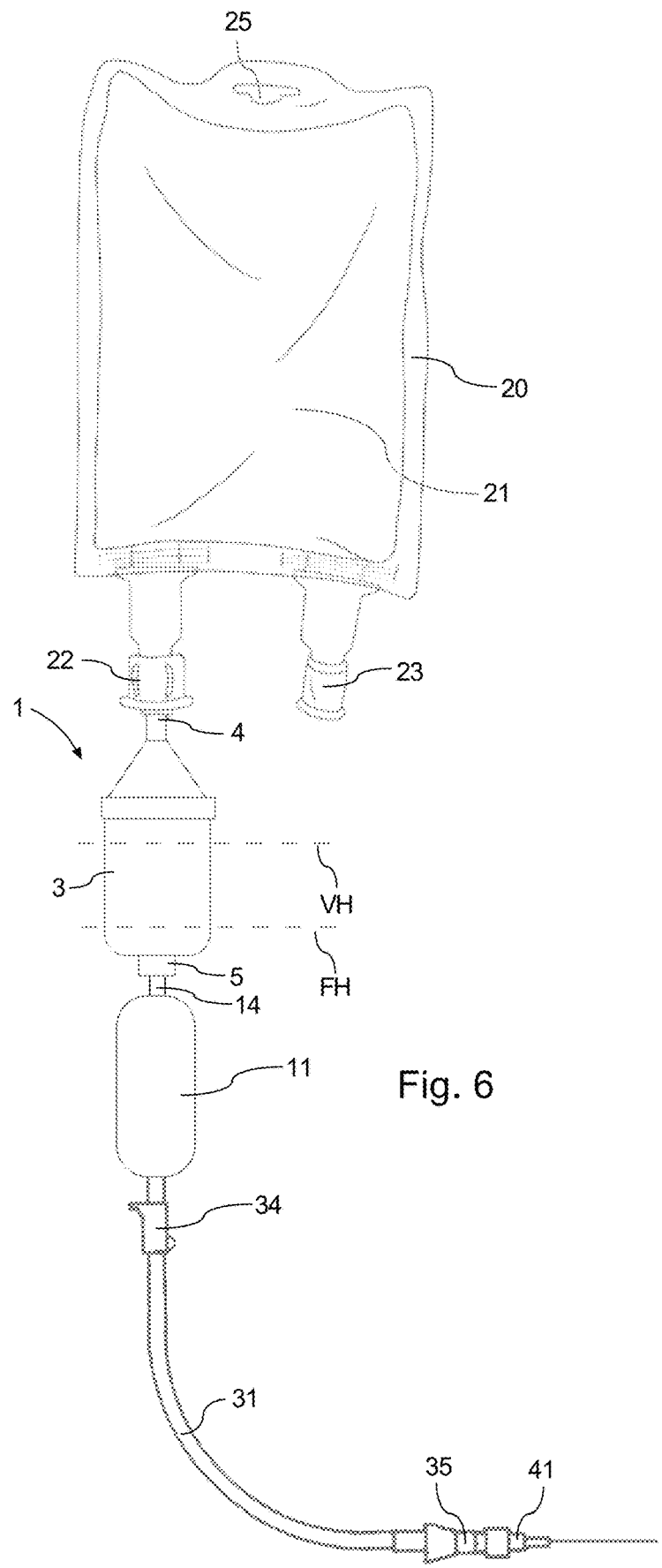
FIG. 6 is an IV infusion set comprising the flushing device of FIG. 1, FIGS. 7 and 8 are elevated views of a flushing device according to another embodiment.

The flushing apparatus 1 comprises a housing 3, a spike 4 forming an inlet coupling component, and an outlet port 5 forming an outlet coupling component. The spike 4 is in FIG. 6 shown inserted with the spike 4 into the outlet port 22 of the collapsible IV solution container 20. The outlet port 22 of the collapsible IV solution container 20 is covered by a membrane to be pierced by the spike 4 of the flushing apparatus 1. The spike 4 forms an inlet coupling component for accessing the content of the collapsible IV liquid container 20 and for receiving a gravity-driven flow of IV liquid from the collapsible IV liquid container 20. The inlet coupling component 4 is arranged, when in use, at an upper end of the flushing apparatus 1. The flushing apparatus 1 comprises an outlet coupling component 5 for coupling to a downstream component 11 and for delivering a gravity-driven flow of IV liquid or flushing liquid to the downstream component 11 of the IV infusion set. The outlet coupling component 5 comprises an outlet port for receiving an IV spike of a downstream component of the IV infusion set, for example, the IV spike 14 of the drip chamber 11. The outlet port of the outlet coupling component 5 is covered by a membrane to be pierced by the IV spike of the downstream component.

The inlet coupling component 4 and the outlet coupling component 5 are both connected to a body of the apparatus 1, and the outlet coupling component 5 is, when in use, arranged at a lower end of the flushing apparatus 1, and preferably, the inlet coupling component 4 is, when in use, arranged at an upper end of the flushing apparatus 1. The body or housing 3 of the flushing apparatus 1 forms a container that defines a rigid and/or noncompressible and/or non-collapsible flushing liquid chamber 2. In this relation, rigid and/or noncompressible and/or non-collapsible is understood to mean that the volume of the flushing liquid chamber 2 does not substantially change during use, i.e. when exposed to pressures and forces that can only be expected during use, to ensure that there is no fluid exchange in or out of the flushing liquid chamber due to deformation of the flushing liquid chamber.

In the shown embodiment, the downstream component 11 is a preferably transparent drip chamber 11. Preferably, an air vent (not shown) is provided at the upper end of the drip chamber 11. The upper end of the drip chamber 11 is provided with a spike 14 that allows the drip chamber 11 to be connected to an upstream component of the IV set, in this embodiment the flushing apparatus 1, by inserting the spike 14 in the outlet connector component 5 of the flushing apparatus 1. The lower end of the drip chamber 11 is preferably provided with an air filter (known also as air stop with Braun® IV sets) to ensure no air enters the downstream tubing which could cause air embolisms in the patient. A tube 31 is provided with an adjustable flow rate roller clamp 34. The tube 31 extends from the drip chamber 11 to a needle connector 35 for example a Luer connector 35. A hypodermic needle 41 can be connected to the needle connector 35. The hypodermic needle 41 is, either directly inserted into a patient or into an IV port that has already been inserted into a patient.

The IV infusion set defines an at least partially gravity-driven fluid flow path for IV liquid that extends from the preferably collapsible container 20 which is positioned as the highest component of the IV infusion set to the needle connector 35 at a lower height. The flow of liquid through the fluid flow path may be assisted by an infusion pump (not shown), thereby resulting in a partially gravity-driven and partially pressure-driven fluid flow through the IV infusion set.

The flushing apparatus 1 comprises a housing or container 3 defining the rigid and/or non-collapsible flushing liquid chamber 2 for containing a flushing liquid and preferably containing the flushing liquid before use. The flushing liquid chamber 2 has an upper end and a lower end. The flushing liquid chamber 2 is a hermetically closed chamber, except for one or more flushing ports 7 at or near the lower end of the flushing liquid chamber 2 and one or more venting ports 17, arranged above the one or more flushing ports 7. In the shown embodiment, there is one flushing port 7 and one venting port 17, but it is understood that there could be a plurality of flushing ports 7 and a plurality of venting ports 17.

The flushing port 7 is fluidically connected to the fluid flow path of the IV infusion set at a flushing height FH (indicated by an interrupted line in the FIGS.). The venting port 17 is fluidically connected to the fluid flow path of the IV infusion set at a venting height VH (indicated by an interrupted line in the FIGS.). The flushing height FH is equal to or lower than the lower end of the collapsible container 20 and the venting height VH is higher than the flushing height FH for simultaneously allowing air from the fluid flow path to enter the flushing liquid chamber 2 via the one or more venting port 17 and flushing liquid from the flushing liquid chamber 2 to enter the fluid flow path via one or more flushing ports 7, when, during use of the IV infusion set, the level of IV liquid in the fluid flow path has become lower than the venting height VH, thereby allowing the flushing liquid chamber 2 to be drained by gravity into the fluid flow path. since the flushing chamber 2, is substantially incompressible and is a closed chamber except for the at least one flushing port 7, flushing liquid, due to its substantially incompressible nature will not leave the flushing chamber 2 through the at least one flushing port 7 unless air from the conduit 6 enters the flushing chamber 2 through the at least one venting port 17. The exchange of flushing liquid and air through at least one flushing port 7 and the at least one venting port 17 happens simultaneously. In this embodiment the fluid flow path is formed by a conduit 6 that extends through the flushing chamber 2 and is formed by a pipe like element that is a part of the flushing apparatus 1. In this embodiment, the conduit 6 is shown as a pipe that extends vertically through the flushing chamber, but it should be understood that the conduit 6 does not need to be straight and does not need to be arranged exactly vertically through the flushing chamber, it merely needs to fluidically connect the upper inlet coupling component 4 to the lower outlet coupling component 5.

In this embodiment the conduit 6, the spike 4 and a lid for closing the upper end of the housing 3 is formed as one integral element (the cap is not an integral element), preferably one integral element that is made from an injection molded polymer. The housing 3, with its open top that is to be closed by the cap/lid is formed as one integral element, preferably one integral element is made from an injected molded polymer.

The at least one flushing port 7 is arranged closer to the lower end of the flushing chamber 2 than to the upper end of the flushing chamber 2. The at least one flushing port 7 is preferably being arranged at or near the lower end of the flushing chamber 2. The at least one venting port 17 is arranged higher than the flushing port 7, and either above or below the height of the upper surface of the flushing liquid in the chamber, which is a level defined by the amount of flushing liquid with which the chamber 2 is filled before use, and with the flushing device 1 in the intended orientation for use with the outlet coupling component 5 arranged at a lower end of the flushing apparatus 1, and the inlet coupling component 4 arranged at an upper end of the flushing apparatus 1.

The least one flushing port 7 is fluidly connected to the fluid flow path (in this embodiment the conduit 6 is part of the fluid flow path) by an always open fluid connection, preferably an always open fluid connection that directly connects at least one flushing port 7 to the fluid flow path. preferably, the at least one flushing port 7 is fluidly connected to the fluid flow path by an always open fluidic connection without any substantial flow restriction or flow control elements. Preferably the at least one flushing port 7 is fluidly connected to the fluid flow path by an always open fluidic connection without any valves, more preferably without any tubing or piping, most preferably the at least one flushing port 7 is being formed by an opening in a wall separating the flushing liquid chamber 2 from the conduit 6 (not shown), or an opening at a flushing conduit 8 that branches off from the conduit as shown in the embodiments of FIGS. 1 to 6. In this embodiment, the flushing conduit 8 is shown extending horizontally, but it is understood that the flushing conduit can be arranged directly or upwardly, and does not need to be straight as shown, but could also be curved.

The least one venting port 17 is fluidly connected to the fluid flow path by an always open fluid connection, preferably an always open fluid connection that directly connects at least one venting port 17 to the fluid flow path. preferably, the at least one flushing port 7 is fluidly connected to the fluid flow path by an always open fluidic connection without any substantial flow restriction or flow control elements. Preferably the at least one venting port 17 is fluidly connected to the fluid flow path by an always open fluidic connection without any valves, more preferably without any tubing or piping, most preferably the at least one venting port 17 is being formed by an opening in a wall separating the flushing liquid chamber 2 from the conduit 6 (not shown), or as an opening of a flushing conduit 18 that branches off from the conduit as shown in the embodiments of FIGS. 1 to 6. In this embodiment, the flushing conduit 18 is shown extending horizontally, but it is understood that the flushing conduit can be arranged directly or upwardly, and does not need to be straight as shown, but could also be curved.

The cross-sectional area of the at least one flushing port 7 is preferably larger than the cross-sectional area of the at least one venting port 17, since the flushing liquid will have a higher restriction to flow through an opening of a given size than air, and in this way the perceived resistance to flow will be the same or at least similar for the air and the flushing liquid.

In the embodiment of FIGS. 1 and 2, the flushing apparatus 1 comprises a conduit 6 that forms part of the flow path of the IV infusion set, and the conduit 6 extends from the spike 4, through the flushing liquid chamber 2 to the outlet port 5. In this embodiment, the pipe that forms the conduit 6 is preferably a rigid pipe that will not substantially deform during use of the apparatus 1.

The conduit 6 is arranged in a main tube extending from the inlet coupling component 4 to the outlet coupling component 5. The at least one flushing port 7 is connected to the main tube by a fluidic connection element 8 connecting the flushing port 7 to the lumen of the main tube. The at least one venting port 17 is connected to the main tube by a fluidic connection element 18 connecting the flushing port 17 to the lumen of the main tube.

In the embodiment of FIGS. 1 and 2, the inlet coupling component 4 and the outlet coupling component 5 are integrally formed with the element 3 that defines the flushing liquid chamber 2. The main body 3 may be provided with one or more circumferential grooves for improving grip on the device by a user and for enhancing the rigidity of the flushing liquid chamber 2.

Generally, flushing liquid chamber 2 is arranged at a height below the IV liquid container 20, or inside the IV liquid container 20.

Preferably, a rigid and/or non-collapsible body 3 that defines the rigid and/or noncompressible flushing liquid chamber 2 and an element defining the conduit 6 are connected to form a single unit. Preferably, the inlet coupling component 4 is rigidly connected to body 3 at an upper end thereof, and the outlet coupling element 5 is rigidly connected to rigid body 3 at the lower end thereof. Preferably, the rigid body is made of transparent material to allow visual inspection of its content.

In the embodiment of FIGS. 1 and 2, and in other conceivable embodiments, the flushing liquid chamber 2 tapers, preferably gradually towards its lower end.

In the embodiment of FIGS. 1 to 6 the conduit 6 extends through the flushing liquid chamber 2, but it should be understood that it is possible to conceive embodiments, in which the flow path does not pass through the flushing chamber 2.

Figure 4:
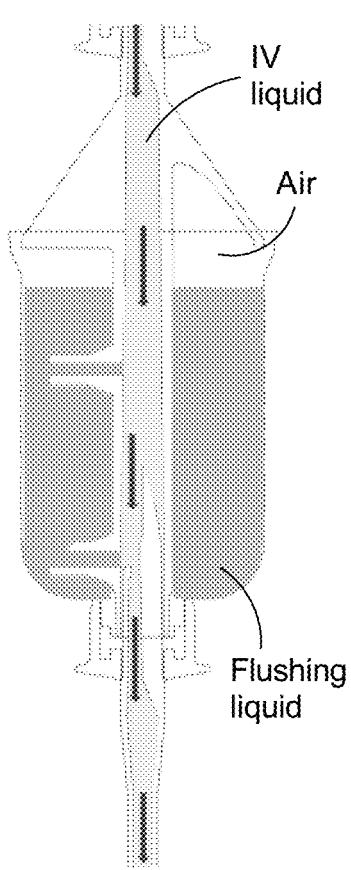
FIG. 4 is a cross-sectional diagrammatic representation of the flushing device of FIG. 1 filled with flushing liquid and connected to an IV bag and to a downstream line, with IV liquid in a portion of a fluid flow path extending through the flushing device.

FIG. 3 illustrates the flushing apparatus 1 filled with flushing liquid but not (yet) connected to any other parts of an IV set. The flushing chamber 2 is filled with a predetermined amount of flushing liquid and there is a predetermined volume of air in the flushing chamber 2 above the flushing liquid. The same applies to the conduit 6, which is filled with flushing liquid to the same level as the chamber, with air being above the flushing liquid. FIG. 4 illustrates the flushing device of 1 connected to an IV liquid container 20 arranged above the flushing device 1, and to a downstream part of an IV set. The IV liquid flows from the IV liquid container 20 through the fluid flow path through the flushing apparatus 1 and into the downstream part of the IV set as indicated by the thick arrows. The flushing liquid remains in the flushing chamber 2 since air cannot enter the flushing chamber 2 when the level of the flushing liquid is as high as in FIG. 4.

Figure 5:
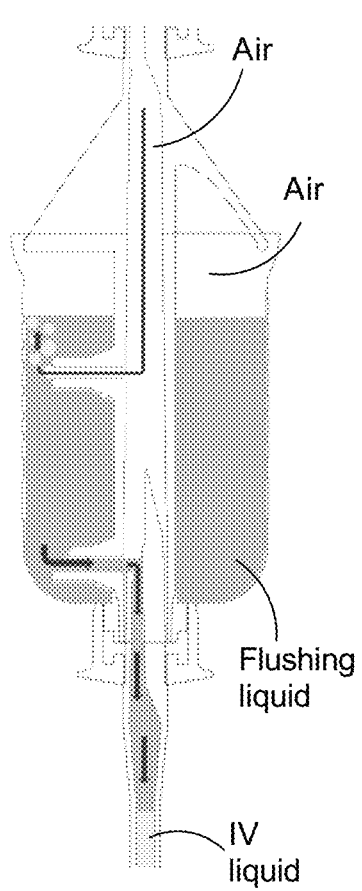
FIG. 5 is a cross-sectional diagrammatic representation of the flushing device of FIG. 1 filled with a reduced amount of flushing liquid and showing air entering the chamber in the flushing device and showing flushing liquid flowing into the flow path for flushing the IV liquid.

FIG. 5 illustrates the flushing apparatus 1 in a subsequent stage, with the flushing chamber 2 is filled with a reduced amount of flushing liquid and the level of the flushing liquid in the flushing chamber 2 being sufficiently low to allow air entering the flushing chamber 2 (shown by the thin arrow and the bubbles in the flushing liquid in the flushing chamber 2) and showing flushing liquid flowing into the flow path for flushing the IV liquid, as indicated by the thick arrows. This process of air flowing into the flushing chamber 2 and flushing liquid flowing into the liquid flow path towards the downstream section of the IV set continues until the level of the flushing liquid in the flushing chamber reach the flushing height defined by the flushing port 7. The initial predetermined amount of flushing liquid in the flushing chamber 2 is selected to be sufficient to flush a substantial amount of IV liquid from the IV set.

Figure 7:
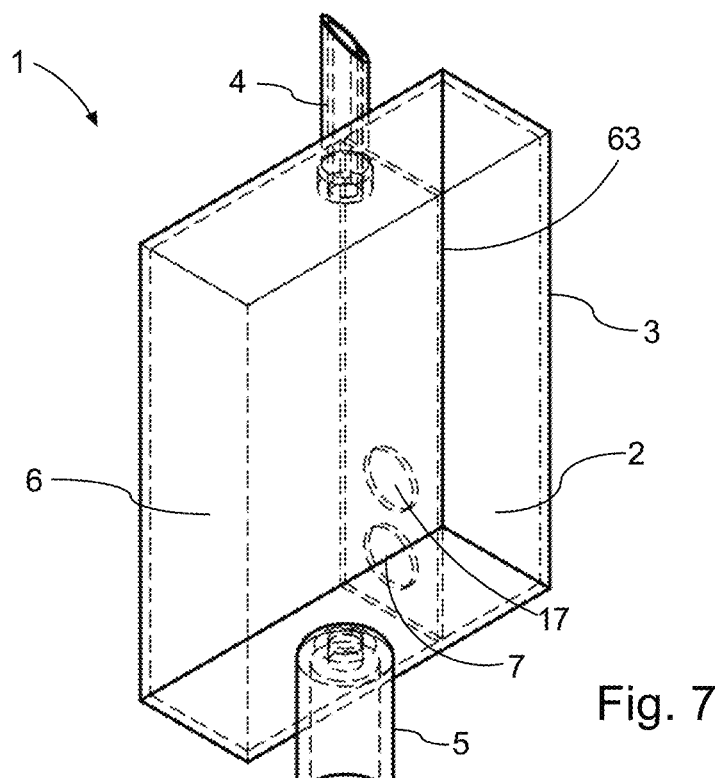
Figure 8:
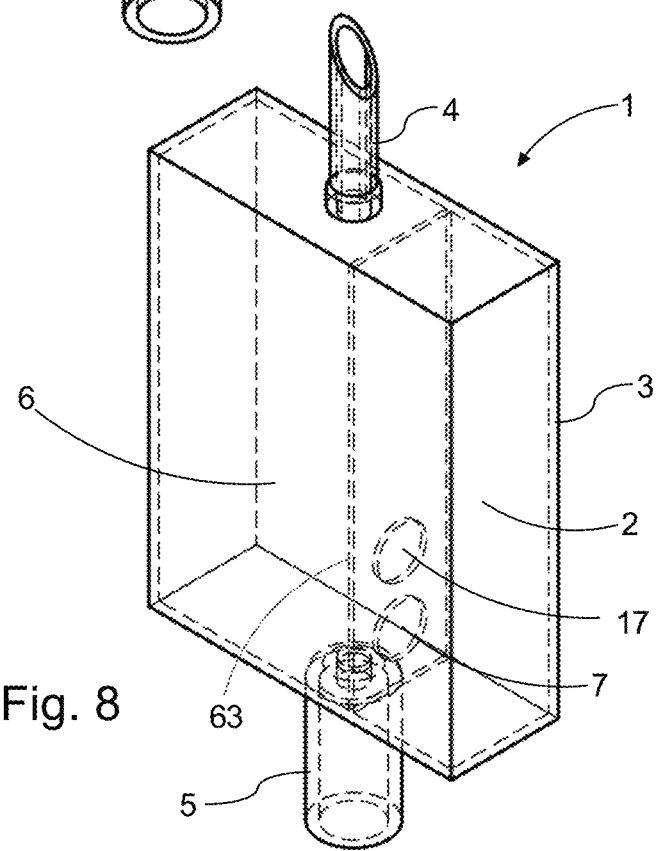

In the embodiments of FIGS. 7 and 8, the conduit does not extend through the flushing liquid chamber 2, but instead extends along the flushing chamber 2. In the embodiments where the conduit 6 does not extend to the flushing chamber 2, the conduit can be made of relatively soft and flexible material so that the conduit is compressible. Thus, the housing 3 of the embodiments of FIGS. 9 and 10 and FIGS. 8 and 9 may comprise a hard and rigid part that encloses the flushing liquid chamber 2 and a relatively soft and flexible part that encloses conduit 6, although the part of encloses conduit 6 can also be rigid.

In an embodiment (shown and explained with reference to FIG. 6), the IV liquid container 20 is provided with an air vent.

In an embodiment, the flushing liquid is saline. In an embodiment, the flushing chamber 2 is prefilled, preferably completely prefilled, with flushing liquid. In an embodiment, the conduit 6 is also prefilled with flushing liquid before use of the flushing apparatus 1 in an IV infusion set.

In an embodiment, the volume of the flushing liquid chamber 2 correlates to a pre-determined flushing volume, preferably a pre-determine flushing volume that substantially corresponds to or slightly exceeds the volume of the flow path in the IV infusion set downstream of the flushing height FH. In an embodiment, the volume of the flushing liquid chamber 2 allows for approximately 15 to 50 mL, preferably approximately 20 to 30 mL, most preferably approximately 25 mL flush to be delivered to the downstream components of the IV infusion set, i.e. the components of the IV infusion set that are downstream of the flushing height FH.

In an embodiment, the IV liquid is a medical solution or a medical solution with a medical substance dissolved in saline.

The flushing port 7 is configured to minimize diffusion and mixing between IV liquid and the flushing liquid. The venting port 17 is configured to only allow air to enter coming from the upstream component of the IV set, e.g. the IV liquid containing 20, and to minimize air entering from the downstream component of the IV infusion set, e.g. the drip chamber 11.

FIGS. 7 and 8 illustrate another embodiment of the flushing device. In this embodiment, structures, and features that are the same or similar to corresponding structures and features previously described or shown herein are denoted by the same reference numeral as previously used for simplicity.

In this embodiment, the conduit 6 extends next to, i.e. adjacent the flushing liquid chamber 2. In this embodiment, both the flushing liquid chamber 6, and the conduit 6 are formed within one housing, separated by a separation wall 63. The flushing port 7 is formed by an opening in the separation wall, and the flushing port 7 is arranged at the lower part of the flushing device 1, close to the lower end of the flushing chamber 2. The venting port 17 is formed by another opening in the separation wall, arranged higher than the opening for the flushing port 7. In FIGS. 7 and 8 the housing that encompasses both the flushing liquid chamber 2 and the conduit 6 is shown as a perfect cuboid, but it should be understood that there is no need for this shape to be completely right-angled and could be carried out by the skilled person in more rounded form. In an embodiment, the complete housing 3 is made of a stiff and/or rigid material, preferably a transparent material to allow visual inspection of its content. In a variation of this embodiment, the portion of the housing 3 that encapsulates the flushing liquid chamber 2 is made of a stiff and/or rigid material, but the rest of the housing is made of flexible material so that the conduit is allowed change shape and/or volume.

Figure 9:
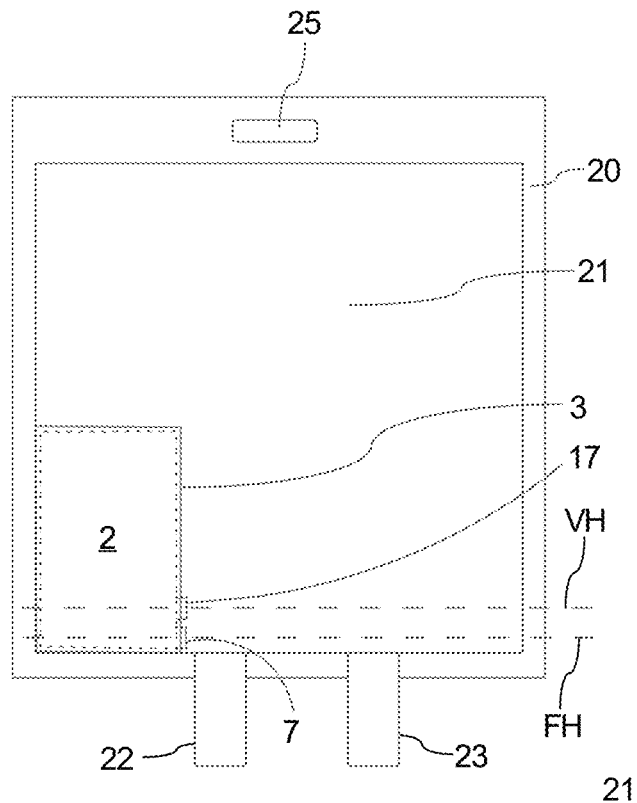
FIG. 9 is a diagrammatic representation of an IV bag comprising a flushing device according to an embodiment.

FIG. 9 shows an embodiment in which the flushing liquid chamber 2 is arranged in the IV liquid bag 20. In this embodiment, structures and features that are the same or similar to corresponding structures and features previously described or shown herein are denoted by the same reference numeral as previously used for simplicity. In this embodiment, the IV liquid container 20 is a bag that defines a collapsible IV liquid chamber 21. The collapsible IV liquid chamber 21 will also contain air. The collapsible infusion liquid chamber 21 has an upper end and a lower end. The infusion bag 20 comprises a container 3 defining the rigid and/or non-collapsible flushing liquid chamber 2 for containing the flushing liquid. The rigid and/or non-collapsible flushing chamber preferably contains already before use of the FE liquid bag. The flushing liquid chamber 2 has an upper end and a lower end. The flushing liquid chamber 2 is a preferably hermetically closed chamber 2, except for at least one flushing port 7 at or near the lower end of the flushing liquid chamber 2 and at least one venting port 17 that is arranged at least slightly higher than the flushing port 7. The at least one flushing port 7 is fluidically connected to the collapsible infusion liquid chamber 21 at or near the lower end of the collapsible infusion liquid chamber 21, and for simultaneously allowing air from the collapsible infusion liquid chamber 21 to enter the flushing liquid chamber 2 via the venting port 17 and flushing liquid from the flushing liquid chamber 2 to enter collapsible infusion liquid chamber 21 via the flushing port 7 when, during use of IV bag 20, the level of IV liquid in the collapsible infusion liquid chamber 21 has become lower than the at least one venting port 17, thereby allowing the flushing liquid chamber 2 to be drained by gravity into the collapsible infusion liquid chamber 21.

The at least one flushing port 7 and the at least one venting port 17 are obstructed by a user destructible barrier, preferably a rupture disk, break-away seal, or puncture membrane, for preventing diffusion between the flushing liquid and the IV liquid before use of the IV liquid bag 20.

The flushing port 7 and the venting port 17 are arranged in a wall separating the infusion liquid chamber 2 from the collapsible IV liquid chamber 21.

The flushing liquid chamber 2 is arranged inside the flexible and collapsible container 20 with the at least one flushing port 7 connecting directly to the IV liquid chamber 21 in the collapsible container 20 at a height at or close to the lower end of the collapsible container 20 with the venting port 17 arranged slightly higher. in an embodiment, not shown, the lower part of the collapsible container 20 is tapered with the flushing liquid chamber 2 arranged in the lowest part of the container to minimize the amount of residual IV liquid at the end of an infusion procedure.

Figure 10:
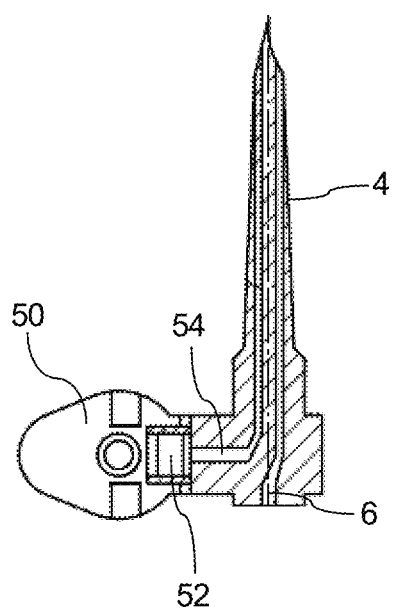
FIG. 10 is a sectional view of another embodiment in which the spike of the flushing device is provided with an air inlet feature.

In an embodiment shown in FIG. 10, the spike 4 of the flushing device 1 is provided with an air inlet, preferably an integral air inlet with an air filter and closure. A channel 54 is integrated into into spike 4, whereas one end of the channel terminates at the upper end of the spike 4 and a second end terminates below the threads of the spike cap. The second opening is covered by an air filter 52 that allows only ambient air to flow into the channel. A closure 50 is situated over the air filter 52 and the second opening of the channel 54 to protect the air filter 52 from ingress of foreign material or contact with liquid and humidity during transport, storage, and use and may pose as a sterile barrier. The closure may be opened when the device is in use to let ambient air flow through the channel in the spike 4 and out the opening that is situated at the upper end of the spike.

For the flushing device 1, to release the flushing solution through the flush port, gas (air) has to enter the flushing chamber 2 through the vent port 17 to effectively displace the volume of the flushing solution in the flushing chamber 2. When the flushing device 1 is used with collapsable IV liquid bags that are filled with a volume of gas in the bag that is lower than the volume of flushing solution contained in the flushing chamber 2, the flushing device 1 only flushes out a volume of flushing liquid that is equal to the gas volume retained in the IV liquid bag and thus does not flush the intended amount of flushing liquid out of the flushing port. In these situations, the closure 50 of the integrated air-inlet may be opened/removed by the user to introduce ambient air into the IV liquid bag, which will subsequently flow through the lumen and vent port into the flushing liquid chamber and displace the intended amount of flushing liquid. The same applies to cases where the device is used with semi-rigid bags that are not filled with a sufficient volume of gas.

In some cases, the device may be used in combination with semi-rigid IV liquid containers in a gravity-driven setup, wherein the IV liquid container is filled with a volume of gas greater than the volume of flushing liquid container in the flushing liquid chamber. During the infusion, the semi-rigid IV liquid container collapses as the volume of IV medication is reduced, due to atmospheric pressure on the container. However, the material properties of the semi-rigid iv liquid container allow the container to not fully collapse and thus create rising negative pressure in the system as compared to the atmospheric pressure. Due to this negative pressure in the semi-rigid IV liquid container, gas may not flow from the bag into the flushing liquid chamber 2 to displace the flushing liquid. In these situations the closure 50 of the integrated air-inlet may be opened or removed by the user to introduce ambient air into the semi-rigid IV liquid container to equalize the pressure differential between the inside of the semi-rigid IV liquid container and the ambient air, thus allowing air into the semi-rigid IV liquid container, which will subsequently flow through the lumen and vent port into the flushing liquid chamber and displace the intended amount of flushing liquid.

In some cases, the device may be used in combination with a rigid IV liquid container, for example, a glass vial, in a pump, or gravity-driven setup. For IV medication to flow out of the rigid IV liquid container, an equivalent volume of air needs to be introduced into the container to displace the IV medication. In these instances, the closure of the integrated air-inlet may be opened or removed by the user to introduce ambient air into the rigid IV liquid container to displace the IV medication. Subsequently, after the full dose of IV medication has been released from the rigid IV liquid container, air from the rigid IV liquid container, can flow through the lumen and vent port into the flushing liquid chamber and displace the intended amount of flushing liquid.

For all the embodiments above, during an IV infusion procedure, the IV liquid container 20 is emptied from IV liquid, and when the level of IV liquid falls below the venting level, air that originates from the IV liquid container 20 enters the flushing liquid chamber 2 through the venting port 17, displacing liquid fluid from the flushing liquid chamber through the flushing port 7 into the fluid flow path.

Below is a non-exhaustive list of the advantages of the above-described IV infusion set, flushing apparatus 1, and the IV liquid bag 20 including the flushing chamber 2.

provision of an automated sequential flushing liquid flush to be used in conjunction with small volume intravenous medicine bags and standard infusion sets.

siginificant reduction of residual medicine in the infusion set.

a closed system with little risk of medicine contamination for staff and reduced risk of infection caused by contamination of the intravenous tube set and access.

an automatic flushing system that can be set up in less than 30 seconds, ensures adherence to patient safety by a spontaneous sequential saline flush, thus securing the minimal risk of catheter occlusion and chemical phlebitis.

ensures that all medication will be delivered at the same rate.

The various aspects and implementations have been described in conjunction with various embodiments herein. However, other variations to the disclosed embodiments can be understood and effected by those skilled in the art in practicing the claimed subject-matter, from a study of the drawings, the disclosure, and the appended claims. In the claims, the word "comprising" does not exclude other elements or steps, and the indefinite article "a" or "an" does not exclude a plurality.

The reference signs used in the claims shall not be construed as limiting the scope. Unless otherwise indicated, the drawings are intended to be read (e.g., cross-hatching, arrangement of parts, proportion, degree, etc.) together with the specification, and are to be considered a portion of the entire written description of this disclosure. As used in the description, the terms "height", "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The invention claimed is:

1. An IV infusion set for administration of an IV liquid, said IV infusion set having an automatic flushing function with a flushing liquid, said IV infusion set defining at least partially gravity-driven fluid flow path for IV liquid that extends from a collapsible IV liquid container (20) for containing IV liquid and air that is, when in use positioned at the highest height of the IV infusion set, to a connector (35) for connecting to a needle (41) for insertion into a patient or to an IV catheter placed in a patient at a lower height, said IV liquid container (20) having an upper end and a lower end, said IV infusion set comprising a body (3) defining a rigid flushing liquid chamber (2)

said flushing liquid chamber (2) having an upper end and a lower end, characterized by said flushing liquid chamber (2) being a closed chamber, except for at least one flushing port (7) at or near the lower end of said flushing liquid chamber (2) and at least one venting port (17) for allowing air from said fluid flow path to enter said flushing liquid chamber (2), said venting port (17) being fluidically connected to said fluid flow path at a vent height (VH), said at least one flushing port (7) being fluidically connected to said fluid flow path at a flushing height (FH), said flushing height (FH) being lower than said vent height (VH), said at least one flushing port (7) forming a permanently open fluidic connection between said flushing liquid chamber (2) and said fluid flow path, said at least one venting port (17) forming a permanently open fluidic connection between said flushing liquid chamber (2) and said fluid flow path, and said flushing height (FH) being equal to or lower than said lower end of said IV liquid container (20) for allowing air from said fluid flow path to enter said flushing liquid chamber (2) via said venting port (17) and simultaneously allowing flushing liquid from said flushing liquid chamber (2) to enter said fluid flow path via said flushing port (7) when, during use of the IV infusion set, the level of IV liquid in the fluid flow path has become lower than said venting height (VH), thereby allowing the flushing liquid chamber (2) to be drained by gravity into the fluid flow path, wherein a cross-sectional area of said venting port (17) is smaller than a cross-sectional area of said flushing port (7).

2. A flushing apparatus (1) for use with an IV infusion set for administration of an IV liquid, the flushing apparatus (1) comprising:

a rigid and/or non-collapsible flushing liquid chamber (2) containing a flushing liquid, said flushing liquid being different from said IV liquid, an inlet coupling component (4) for accessing an IV liquid container (20) and for receiving an at least partially gravity-driven flow of IV liquid from the IV liquid container (20), the inlet coupling component (4) being arranged, when in use, at an upper end of the flushing apparatus (1), an outlet coupling component (5) for coupling to a downstream component (11) and for delivering a gravity driven flow of IV liquid and flushing liquid to the downstream component (11), the outlet coupling component (5) being arranged, when in use, at a lower end of the flushing apparatus (1), and a conduit (6) fluidically connecting the inlet coupling component (4) to the outlet coupling component (5), said flushing liquid chamber (2) having an upper end and a lower end, characterized by said flushing liquid chamber (2) being a closed chamber, except for at least one flushing port (7) at or near the lower end of said flushing liquid chamber (2) and at least one venting port (17) for allowing air from said conduit (6) to enter said flushing liquid chamber (2), said venting port (17) being fluidically connected to said conduit (6) at a vent height (VH), said at least one flushing port (7) forming a permanently open fluidic connection between said flushing liquid chamber (2) and said conduit (6), said at least one venting port (17) forming a permanently open fluidic connection between said flushing liquid chamber (2) and said fluid conduit (6), said at least one flushing port (7) being fluidically connected to said conduit (6) at a flushing height (FH) and said flushing height (FH) being lower than said vent height (VH), for simultaneously allowing air from said conduit (6) to enter said flushing liquid chamber (2) via said venting port (17) and flushing liquid from said flushing liquid chamber (2) to enter said conduit (6) via said flushing port (7), when, during use of flushing apparatus (1), the level of IV liquid in the conduit (6) has become lower than said venting height (VH), thereby allowing the flushing liquid chamber (2) to be drained by gravity into the conduit (6).

3. The apparatus (1) according to claim 2, wherein the conduit (6) extends through the flushing liquid chamber (2).

4. The apparatus (1) according to claim 2, wherein the at least one flushing port (7) is arranged closer to said lower end of the flushing liquid chamber (2) than to the upper end of the flushing liquid chamber (2), the at least flushing port (7) preferably being arranged at or near the lower end of the flushing liquid chamber (2).

5. The apparatus (1) according to claim 2, wherein the at least one flushing port (7) and/or said venting port (17) comprises an opening in a wall of the conduit (6).

6. The apparatus (1) according to a claim 2, wherein at least a portion of the conduit (6) is inside a main tube that extends from said inlet coupling component (4) to said outlet coupling component (5), and wherein the at least one flushing port (7) and/or the at least one venting port (17) is preferably connected to said main tube.

7. The apparatus (1) according to claim 2, wherein the inlet coupling component (4) comprises an IV spike, and/or wherein the outlet coupling component (5) comprises a port for receiving an IV spike.

8. The apparatus (1) according to claim 2, wherein the conduit (6), the inlet coupling component (4) and/or the outlet coupling component (5) are integrally formed with a body (3) that defines the flushing liquid chamber (2).

9. The IV infusion set according to claim 2, wherein said at least one flushing port (7) and/or said at least one venting port (17) is an always open fluidic connection that directly connects said flushing port (7) to the fluid flow path, preferably said at least one flushing port (7) and/or said at least one venting port (17) being formed by an opening in a wall separating said flushing liquid chamber (2) from said fluid flow path.

10. The IV infusion set according to claim 2, wherein said at least one flushing port (7) and said at least one venting port (17) forms one or more of:

a permanently open fluidic connection without substantial flow restriction, a permanently open fluidic connection without flow control elements, a permanently open fluidic connection without valves, a permanently open fluidic connection comprising neither tubing nor piping.

11. The apparatus (1) according to claim 2, wherein the apparatus (1) comprises a fluid flow path for IV infusion liquid to pass through the apparatus (1), said conduit (6) forming part of said fluid flow path.

12. An IV infusion set comprising an apparatus (1) according to claim 2.

13. An IV infusion set for administration of an IV liquid, said IV infusion set having an automatic flushing function with a flushing liquid, said IV infusion set defining at least partially gravity-driven fluid flow path for IV liquid that extends from a collapsible IV liquid container (20) for containing IV liquid and air that is, when in use positioned at the highest height of the IV infusion set, to a connector (35) for connecting to a needle (41) for insertion into a patient or to an IV catheter placed in a patient at a lower height, said IV liquid container (20) having an upper end and a lower end, said IV infusion set comprising a body (3) defining a rigid flushing liquid chamber (2)

said flushing liquid chamber (2) having an upper end and a lower end, characterized by said flushing liquid chamber (2) being a closed chamber, except for at least one flushing port (7) at or near the lower end of said flushing liquid chamber (2) and at least one venting port (17) for allowing air from said fluid flow path to enter said flushing liquid chamber (2), said venting port (17) being fluidically connected to said fluid flow path at a vent height (VH), said at least one flushing port (7) being fluidically connected to said fluid flow path at a flushing height (FH), said flushing height (FH) being lower than said vent height (VH), said at least one flushing port (7) forming a permanently open fluidic connection between said flushing liquid chamber (2) and said fluid flow path, said at least one venting port (17) forming a permanently open fluidic connection between said flushing liquid chamber (2) and said fluid flow path, and said flushing height (FH) being equal to or lower than said lower end of said IV liquid container (20) for allowing air from said fluid flow path to enter said flushing liquid chamber (2) via said venting port (17) and simultaneously allowing flushing liquid from said flushing liquid chamber (2) to enter said fluid flow path via said flushing port (7) when, during use of the IV infusion set, the level of IV liquid in the fluid flow path has become lower than said venting height (VH), thereby allowing the flushing liquid chamber (2) to be drained by gravity into the fluid flow path, wherein the fluid flow path for IV liquid comprises a conduit (6) extending from an inlet coupling at the upper end to an outlet coupling at said lower end.

14. An IV infusion set for administration of an IV liquid, said IV infusion set having an automatic flushing function with a flushing liquid, said IV infusion set defining at least partially gravity-driven fluid flow path for IV liquid that extends from a collapsible IV liquid container (20) for containing IV liquid and air that is, when in use positioned at the highest height of the IV infusion set, to a connector (35) for connecting to a needle (41) for insertion into a patient or to an IV catheter placed in a patient at a lower height, said IV liquid container (20) having an upper end and a lower end, said IV infusion set comprising a body (3) defining a rigid flushing liquid chamber (2)

said flushing liquid chamber (2) having an upper end and a lower end, characterized by said flushing liquid chamber (2) being a closed chamber, except for at least one flushing port (7) at or near the lower end of said flushing liquid chamber (2) and at least one venting port (17) for allowing air from said fluid flow path to enter said flushing liquid chamber (2), said venting port (17) being fluidically connected to said fluid flow path at a vent height (VH), said at least one flushing port (7) being fluidically connected to said fluid flow path at a flushing height (FH), said flushing height (FH) being lower than said vent height (VH), said at least one flushing port (7) forming a permanently open fluidic connection between said flushing liquid chamber (2) and said fluid flow path, said at least one venting port (17) forming a permanently open fluidic connection between said flushing liquid chamber (2) and said fluid flow path, and said flushing height (FH) being equal to or lower than said lower end of said IV liquid container (20) for allowing air from said fluid flow path to enter said flushing liquid chamber (2) via said venting port (17) and simultaneously allowing flushing liquid from said flushing liquid chamber (2) to enter said fluid flow path via said flushing port (7) when, during use of the IV infusion set, the level of IV liquid in the fluid flow path has become lower than said venting height (VH), thereby allowing the flushing liquid chamber (2) to be drained by gravity into the fluid flow path, wherein said fluid flow path for IV liquid comprises a conduit (6) extending from said upper end to said lower end of the flushing chamber.

15. An IV infusion set for administration of an IV liquid, said IV infusion set having an automatic flushing function with a flushing liquid, said IV infusion set defining at least partially gravity-driven fluid flow path for IV liquid that extends from a collapsible IV liquid container (20) for containing IV liquid and air that is, when in use positioned at the highest height of the IV infusion set, to a connector (35) for connecting to a needle (41) for insertion into a patient or to an IV catheter placed in a patient at a lower height, said IV liquid container (20) having an upper end and a lower end, said IV infusion set comprising a body (3) defining a rigid flushing liquid chamber (2)

said flushing liquid chamber (2) having an upper end and a lower end, characterized by said flushing liquid chamber (2) being a closed chamber, except for at least one flushing port (7) at or near the lower end of said flushing liquid chamber (2) and at least one venting port (17) for allowing air from said fluid flow path to enter said flushing liquid chamber (2), said venting port (17) being fluidically connected to said fluid flow path at a vent height (VH), said at least one flushing port (7) being fluidically connected to said fluid flow path at a flushing height (FH), said flushing height (FH) being lower than said vent height (VH), said at least one flushing port (7) forming a permanently open fluidic connection between said flushing liquid chamber (2) and said fluid flow path, said at least one venting port (17) forming a permanently open fluidic connection between said flushing liquid chamber (2) and said fluid flow path, and said flushing height (FH) being equal to or lower than said lower end of said IV liquid container (20) for allowing air from said fluid flow path to enter said flushing liquid chamber (2) via said venting port (17) and simultaneously allowing flushing liquid from said flushing liquid chamber (2) to enter said fluid flow path via said flushing port (7) when, during use of the IV infusion set, the level of IV liquid in the fluid flow path has become lower than said venting height (VH), thereby allowing the flushing liquid chamber (2) to be drained by gravity into the fluid flow path, wherein the IV liquid comprises medicine, and the flushing fluid is a fluid different from the IV liquid.

16. An IV infusion set for administration of an IV liquid, said IV infusion set having an automatic flushing function with a flushing liquid, said IV infusion set defining at least partially gravity-driven fluid flow path for IV liquid that extends from a collapsible IV liquid container (20) for containing IV liquid and air that is, when in use positioned at the highest height of the IV infusion set, to a connector (35) for connecting to a needle (41) for insertion into a patient or to an IV catheter placed in a patient at a lower height, said IV liquid container (20) having an upper end and a lower end, said IV infusion set comprising a body (3) defining a rigid flushing liquid chamber (2)

said flushing liquid chamber (2) having an upper end and a lower end, characterized by said flushing liquid chamber (2) being a closed chamber, except for at least one flushing port (7) at or near the lower end of said flushing liquid chamber (2) and at least one venting port (17) for allowing air from said fluid flow path to enter said flushing liquid chamber (2), said venting port (17) being fluidically connected to said fluid flow path at a vent height (VH), said at least one flushing port (7) being fluidically connected to said fluid flow path at a flushing height (FH), said flushing height (FH) being lower than said vent height (VH), said at least one flushing port (7) forming a permanently open fluidic connection between said flushing liquid chamber (2) and said fluid flow path, said at least one venting port (17) forming a permanently open fluidic connection between said flushing liquid chamber (2) and said fluid flow path, and said flushing height (FH) being equal to or lower than said lower end of said IV liquid container (20) for allowing air from said fluid flow path to enter said flushing liquid chamber (2) via said venting port (17) and simultaneously allowing flushing liquid from said flushing liquid chamber (2) to enter said fluid flow path via said flushing port (7) when, during use of the IV infusion set, the level of IV liquid in the fluid flow path has become lower than said venting height (VH), thereby allowing the flushing liquid chamber (2) to be drained by gravity into the fluid flow path,
wherein the IV liquid comprises medicine, and the flushing fluid is a saline.

* * * * *